US006962942B2

(12) United States Patent
Miller et al.

(10) Patent No.: US 6,962,942 B2
(45) Date of Patent: Nov. 8, 2005

(54) AZACYCLOALKANONE SERINE PROTEASE INHIBITORS

(75) Inventors: Scott C. Miller, Longmont, CO (US); Juan José Marugán Sánchez, Exton, PA (US); Kristin D. Haslow, Downingtown, PA (US); Jonathan Hall, Snyder, NY (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 53 days.

(21) Appl. No.: 10/243,938

(22) Filed: Sep. 16, 2002

(65) Prior Publication Data

US 2003/0109517 A1 Jun. 12, 2003

Related U.S. Application Data

(62) Division of application No. 09/661,327, filed on Sep. 13, 2000, now Pat. No. 6,469,029.
(60) Provisional application No. 60/153,236, filed on Sep. 13, 1999.

(51) Int. Cl.$^7$ ...................... A61K 31/505; A61K 31/44; A61K 31/47; A61K 31/40; A61P 9/00; C07D 239/02; C07D 491/00; C07D 498/00; C07D 215/00; C07D 401/00

(52) U.S. Cl. ...................... 514/424; 514/256; 514/291; 514/302; 514/312; 514/313; 514/314; 514/333; 514/336; 514/337; 514/339; 514/341; 514/343; 514/393; 514/397; 514/411; 514/414; 514/422; 544/335; 546/90; 546/115; 546/153; 546/157; 546/159; 546/169; 546/171; 546/173; 546/175; 546/256; 546/273.1; 546/274.1; 546/277.4; 546/277.7; 546/278.1; 546/278.4; 548/303.1; 548/314.7; 548/430; 548/431; 548/467; 548/525; 548/526; 548/527; 548/550

(58) Field of Search ...................... 514/256, 291, 514/302, 312, 313, 314, 333, 336, 337, 339, 341, 343, 393, 397, 411, 414, 422, 424; 544/335; 546/90, 115, 153, 157, 159, 169, 171, 173, 175, 256, 273.1, 274.1, 277.4, 277.7, 278.1, 278.4; 548/303.1, 314.7, 430, 431, 467, 525, 526, 527, 550

(56) References Cited

U.S. PATENT DOCUMENTS

| 4,727,064 A | 2/1988 | Pitha ............................ 514/58 |
| 4,764,604 A | 8/1988 | Müller ......................... 536/103 |
| 5,024,998 A | 6/1991 | Bodor ........................... 514/58 |
| 5,385,885 A | 1/1995 | Gasic et al. ................... 514/12 |
| 5,703,208 A | 12/1997 | Semple et al. ............... 530/331 |
| 5,891,909 A | 4/1999 | Soll et al. .................... 514/517 |
| 6,037,356 A | 3/2000 | Lu et al. ...................... 514/349 |

FOREIGN PATENT DOCUMENTS

| EP | 0 526 877 A2 | 2/1993 |
| JP | 09165370 | 6/1997 |
| WO | WO 93/01208 A1 | 1/1993 |
| WO | WO 94/20535 | 9/1994 |
| WO | WO 95/35311 A1 | 12/1995 |
| WO | WO 97/01338 A1 | 1/1997 |
| WO | WO 97/30073 | 8/1997 |
| WO | WO 97/30708 | 8/1997 |
| WO | WO 98/16523 | 4/1998 |
| WO | WO 99/07731 | 2/1999 |
| WO | WO 99/07732 | 2/1999 |

OTHER PUBLICATIONS

Bromberg, M.E., et al., "Cancer and Blood Coagulation: Molecular Aspects," *Cancer J.* 5:132–138, Scientific American, Ltd. (May/Jun. 1999).

Cirino, G., et al., "Factor Xa as an Interface Between Coagulation and Inflammation. Molecular Mimicry of Factor Xa Association with Effector Cell Protease Receptor–1 Induces Acute Inflammation In Vivo," *J. Clin. Invest.* 99:2446–2451, The American Society for Clinical Investigation, Inc. (1997).

Edmunds, J.J., and Rapundalo, S.T., "Thrombin and Factor Xa Inhibition," *Ann. Rep. Med. Chem.* 31:51–60, Academic Press, Inc. (1996).

Esmon, C.T., "Role of Coagulation Inhibitors in Inflammation," *Thromb. Haemost.* 86:51–56, Schattauer GmbH, Stuttgart (Jul. 2001).

(Continued)

*Primary Examiner*—Brenda Coleman
(74) *Attorney, Agent, or Firm*—Woodcock Washburn LLP

(57) ABSTRACT

The present invention is directed to non-peptidic factor Xa inhibitors which are useful for the treatment of arterial and venous thrombotic occlusive disorders, inflammation, cancer, and neurodegenerative diseases. The factor Xa inhibitors provide compounds having Formula I:

I or pharmaceutically acceptable salts thereof; wherein

Q is phenyl, benzyl, pyridyl, thienyl, indolyl, quinolinyl, benzothienyl, biphenylyl, or imidazolyl; any of which can include one or more optional substituents independently selected from halo, trifluoromethyl, hydroxy, amino, nitro, cyano, $C_1$ alkoxy, $C_{1-3}$ alkyl, methylenedioxy, carboxamido, acetamido, or amidino;

X is methylene, carbonyl, or sulfonyl; Z is methylene, ethylene, or propylene; M is methylene or ethylene; and $R^1$ $R^2$ and $R^3$ are independently hydrogen or $C_{1-3}$ alkyl.

24 Claims, No Drawings

OTHER PUBLICATIONS

Haas, C., et al., "Proteolysis of Alzheimer's disease β–amyloid precursor protein by factor Xa," *Biochim. Biophys. Acta* 1343:85–94, Elsevier Science B.V. (1997).

Ornstein, D.L., and Zacharski, L.R., "Treatment of Cancer with Anticoagulants: Rationale in the Treatment of Melanoma," *Int. J. Hematol.* 73:157–161, Carden Jennings Publishing (Feb. 2001).

CAPLUS Accession No. 1997:479333, Document No. 127:121652, CAPLUS English lanugage abstract, American Chemical Society, for JP 09165370 (Document AL3), Jun. 1997.

CAPLUS Accession No. 1993:428019, Document No. 119:28019, CAPLUS English language abstract, American Chemical Society, for WO 93/01208 (Document AN2), Jan. 1993.

European Patent Office: Patent Abstracts of Japan, English language abstract, Japanese Patent Office, for JP 09165370 (Document AL3), Jun. 1997.

International Search Report for International Application No. PCT/US00/25006 mailed on Dec. 13, 2000.

Dialog File 351, WPI Accession No. 1993–009740/199302, Derwent WPI English language abstract for WO 93/01208 (Document AN2), Jan. 1993.

Adang, A.E.P., et al., "Novel Acylguanidine Containing Thrombin Inhibitors with Reduced Basicity at the P1 Moiety," *Bioorg. Med. Chem. Lett.* 8:3603–3608 (Dec. 1998).

Brown, F.J., et al., "Design of Orally Active, Non–Peptidic Inhibitors of Human Leukocyte Elastase," *J. Med. Chem.* 37:1259–1261 (Apr. 1994).

Coughlin, S.R., "Molecular Mechanisms of Thrombin Signaling," *Seminars in Hematology* 31:270–277 (Oct. 1994).

Cuypers, H.T., et al., "Sulfhydryl Content of Bovine Eye Lens Leucine Aminopeptidase," *J. Biol. Chem.* 257:7086–7091 (Jun. 1982).

Freidinger, R.M., et al., "Protected Lactam–Bridged Dipeptides for Use as Conformational Constraints in Peptides," *J. Org. Chem.* 47:104–109 (Jan. 1982).

Glaeson, G., "Synthetic Peptides and Peptidomimetics as Substrates and Inhibitors of Thrombin and Other Proteases in the Blood Coagulation System,"0 *Blood Coagulation and Fibrinolysis* 5:411–436 (Jun. 1994).

Hara, T., et al., "DX–9065a, a New Synthetic, Potent Anticoagulant and Selective Inhibitor for Factor Xa," *Thrombosis Haemostasis* 71:314–319 (Mar. 1994).

Harker, L.A., "Strategies for Inhibiting the Effects of Thrombin," *Blood Coagulation and Fibrinolysis* 5:S47–S58 (Jan. 1994).

Kawasaki, T., et al., "Effect of a Synthetic Factor Xa Inhibitor, YM–60828, on Blood Vessel Patency in Combination with a Thrombolytic Agent and on Blood Loss from the Operation Site in a Rat Model of Arterial Thrombosis," *Thromb. Haemost.* 79:859–864 (Apr. 1998).

Krishnan, R., et al., "Highly Selective Mechanism–Based Thrombin Inhibitors: Structures of Thrombin and Trypsin Inhibited with Rigid Peptidyl Aldehydes," *Biochemistry* 37:12094–12103 (Nov. 1998).

Lefkovits, J., et al., "Direct Thrombin Inhibitors in Cardiovascular Medicine," *Circulation* 90:1522–1536 (Sep. 1994).

Levy, O.E., et al., "Potent and Selective Thrombin Inhibitors Incorporating the Constrained Arginine Mimic L–3–Piperidyl(N–guanidino)alanine at P1," *J. Med. Chem.* 39:4527–4530 (Nov. 1996).

Lu, T., et al., "In Vitro Evaluation and Crystallographic Analysis of a New Class of Selective, Non–Amide–Based Thrombin Inhibitors," *Bioorg. Med. Chem. Lett.* 8:1595–1600 (Jul. 1998).

Lu, T., et al., "Structure–Activity and Crystallographic Analysis of a New Class of Non–amide–Based Thrombin Inhibitor," *Bioorg. Med. Chem. Lett.* 10:79–82 (Jan. 2000).

Markwardt, F., "Inventory of Coagulation Inhibitors from Animals Feeding on Blood," *Thrombosis and Haemostasis* 72:477–480 (Sep. 1994).

Meilott, M.J., et al., "Acceleration of Recombinant Tissue–Type Plasminogen Activator–Induced Reperfusion and Prevention of Reocclusion by Recombinant Antistasin, a Selective Factor Xa Inhibitor, in a Canine Model of Femoral Arterial Thrombosis," *Circulation Res.* 70:1152–1160 (Jun. 1992).

Morishima, Y., et al., "Antithrombotic and Hemorrhagic Effects of DX–9065a, a Direct and Selective Factor Xa Inhibitor: Comparison with a Direct Thrombin Inhibitor and Antithrombin III–Dependent Anticoagulants," *Thromb. Haemost.* 78:1366–1371 (Nov. 1997).

Nagahara, T., et al., "Dibasic (Amidinoaryl)propanoic Acid Derivatives as Novel Blood Coagulation Factor Xa Inhibitors," *J. Med. Chem.* 37:1200–1207 (Apr. 1994).

Nutt, R.F., et al., "Discovery and Development of Potent, Selective and Orally Bioavailable Thrombin Inhibitors," *Peptides 1996 Proceedings of the Twenty–Fourth Eurpean Peptide Symposium*, eds. Ramage, R. and Epton R., Sep. 8–13, 1996, Mayflower Scientific Ltd., 71–74.

Prasa, D., et al., "Inhibition of Thrombin Generation in Plasma by Inhibitors of Factor Xa," *Thromb. Haemost.* 78:1215–1220 (Oct. 1997).

Ragosta, M., et al., "Specific Factor Xa Inhibition Reduces Restenosis After Balloon Angioplasty of Atheroslerotic Femoral Arteries in Rabbits," *Circulation* 89:1262–1271 (Mar. 1994).

Rewinkel, J.B.M., et al., "Strategies and Progress Towards the Ideal Orally Active Thrombin Inhibitor," *Curr. Pharm. Des.* 5:1043–1075 (Dec. 1999).

Scholtz, J.M., et al., "A Convenient Differential Protection Strategy for Functional Group Manipulation of Aspartic and Glutamic Acids," *Synthesis* 477–570 (Jul. 1989).

Semple, J.E., et al., "Design and Construction of Novel Thrombin Inhibitors Featuring P3–P4 Quaternary Lactam Dipeptide Surrogates," *Bioorg. Med. Chem. Lett.* 8:2501–2506 (Sep. 1998).

Semple, J.E., et al., "Design, Synthesis, and Evolution of a Novel, Selective, and Orally Bioavailable Class of Thrombin Inhibitors: P1–Argininal Derivatives Incorporating P3–P4 Lactam Sulfonamide Moieties," *J. Med. Chem.* 39:4531–4536 (Nov. 1996).

Seymour, J.L., et al., "Ecotin is a Potent Anticoagulant and Reversible Tight–Binding Inhibitor of Factor Xa," *Biochemistry* 33:3949–3958 (Apr. 1994).

Sitko, G.R., et al., "Conjuctive Enhancement of Enzymatic Thrombolysis and Prevention of Thrombotic Reocclusion with the Selective Factor Xa Inhibitor, Tick Anticoagulant Peptide," *Circulation* 85:805–815 (Feb. 1992).

Soll, R.M., et al., "Amidinohydrazones as Guanidine Bioisosteres: Application to a New Class of Potent, Selective and Orally Bioavailable, Non–amide–Based Small–Molecule Thrombin Inhibitors," *Bioorg. Med. Chem. Lett. 10*:1–4(Jan. 2000).

Stürzebecher, J., et al., "Synthetic Inhibitors of Bovine Factor Xa and Thrombin Comparison of Their Anticoagulant Efficiency," *Thrombosis Res. 54*:245–252 (May 1989).

Tapparelli, C., et al., "Synthetic Low–molecular Weight Thrombin Inhibitors: Molecular Design and Pharmacological Profile," *Trends Pharmacolog. Sci. 14*:366–376 (Oct. 1993).

Tidwell, R.R., et al., "Strategies for Anticoagulation with Synthetic Protease Inhibitors. Xa Inhibitors Versus Thrombin Inhibitors," *Thrombosis Res. 19*:339–349 (Aug. 1980).

Yamazaki, M., et al., "Effects of DX–9065a, an Orally Active, Newly Synthesized and Specific Inhibitor of Factor Xa, against Experimental Disseminated Intravascular Coagulation in Rats," *Thrombosis Haemostasis 72*:393–396 (Sep. 1994).

Yokoyama, T., et al., "Antithrombotic Effects of Orally Active Synthetic Antagonist of Activated Factor X in Nonhuman Primates," *Circulation 92*:485–491 (Aug. 1995).

AZACYCLOALKANONE SERINE PROTEASE INHIBITORS

This application is a divisional of U.S. patent application Ser. No. 09/661,327, filed Sep. 13, 2000, now U.S. Pat. No. 6,469,029, which claims benefit under 35 U.S.C. § 119(e) of U.S. Provisional Application No. 60/153,236, filed Sep. 13, 1999, the contents of which are fully incorporated by reference herein.

BACKGROUND OF THE INVENTION

1. Field of the Invention

The present invention relates to novel compounds that function as proteolytic enzyme inhibitors, and particularly to a new class of inhibitors of thrombin production via factor Xa inhibition, their pharmaceutically acceptable salts, and pharmaceutically acceptable compositions thereof.

2. Related Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs*, Sandler, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons. Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4):270–277 (1994)), and autoamplifies its own production through a feedback mechanism. Thus, inhibitors of thrombin function have therapeutic potential in a host of cardiovascular and non-cardiovascular diseases.

Factor Xa is another serine protease in the coagulation pathway. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (*Suppl* 1):S47–S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522–1536 (1994); Harker, *Blood Coagulation and Fibrinolysis* 5 (*Suppl* 1):S47–S58 (1994)).

Direct thrombin inhibitors of various structural classes have been identified recently (Tapparelli et al., *Trends in Pharmacological Sciences* 14:366–376 (1993); Claeson, *Blood Coagulation and Fibrinolysis* 5:411–436 (1994); Lefkovits and Topol, *Circulation* 90(3):1522–1536 (1994)). Representative compounds that act by inhibiting the active site of thrombin include the α-chloroketone D-phenylalanyl-L-prolyl-L-arginyl chloromethylketone (PPACK), the boroarginine DUP714, the peptide arginal GYKI 14766, the cyclic peptides cyclotheonamides A and B, the benzamidine NAPAP, and the arylsulphonylarginine argatroban. The thrombin inhibitory peptides hirudin and hirulogs additionally span through the active and exosite domains of thrombin. The peptide hirugen and single-stranded DNA aptamers inhibit thrombin through exosite occupancy. These classes of antithrombotic agents still suffer from one or more of the following liabilities: (1) poor oral bioavailability due to the peptidic or oligonucleotidic nature of these agents, or high molecular weight or charged nature of the agents; (2) excessive bleeding complications; (3) poor selectivity towards thrombin versus other serine proteases (that may lead to severe and sometimes fatal hypotension and respiratory depression in animal models); (4) liver toxicity; or (5) cost effectiveness.

An alternative approach for inhibiting thrombin function is to inhibit factor Xa. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (*Suppl* 1):S47–S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3): 1522–1536(1994); Harker, *Blood Coagulation and Fibrinolysis* (*Suppl* 1):S47–S58 (1994)). Indeed, continuous generation of new thrombin rather than reexposure of preformed clot-bound thrombin is thought to be responsible in part for the phenomenon of reocclusion since markers of thrombin generation have been found to increase during and after thrombolytic treatment for myocardial infarction. Thus, it is now believed that increased thrombin activity associated with thrombolysis is due at least in part to new thrombin generation.

Specific protein factor Xa inhibitors, such as the leech-derived, 119-amino acid protein antistasin and the soft tick-derived protein TAP (tick anticoagulant peptide) accelerated clot lysis and prevented reocclusion when given as adjuncts to thrombolysis (Mellott et al., *Circulation Research* 70:1152–1160 (1992); Sitko et al., *Circulation* 85:805–815 (1992)). U.S. Pat. No. 5,385,885, issued Jan. 31, 1995, discloses smooth muscle cell proliferation inhibitory activity of both TAP and antistasin. Additionally, TAP and antistasin have been shown to reduce experimental restenosis. These results suggest that factor Xa may play a role in the restenosis process through its effects upon thrombus formation or through its mitogenic potential (Ragosta et al., *Circulation* 89:1262–1271 (1994)). The peptide ecotin is another selective, reversible, tight-binding inhibitor of factor Xa that exhibits potent anticoagulant activity (Seymour et al., *Biochemistry* 33:3949–3959 (1994); PCT Published Application WO 94/20535, published Sep. 14, 1994). Ixodidae, argasin, and ancylostomatin are other representative peptidic factor Xa inhibitors isolated from animals that feed on blood (Markwardt, *Thrombosis and Hemostasis* 72:477–479 (1994)).

Non-peptide diamidino derivatives, such as (+)-(2S)-2-[4-[[(3S)-1-acetimidoyl-3-pyrrolidinyl]oxy]phenyl]-3-[7-amidino-2-naphthyl]propanoic acid hydrochloride pentahydrate (DX-9065a), exhibit anticoagulant activity (Tidwell et al., *Thrombosis Research* 19:339–349 (1980); Yamazaki et al., *Thrombosis and Hemostasis* 72:393–395 (1994); Hara et al., *Thrombosis and Hemostasis* 71:314–319 (1994); Nagahara et al., *Journal of Medicinal Chemistry* 37:1200–1207 (1994)). Synthetic amidino derivatives of phenylalanine and cycloheptanone have also shown potent factor Xa inhibition (Sturzebecher et al., *Thrombosis Research* 54:245–252 (1989)).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

SUMMARY OF THE INVENTION

The present invention is directed to novel compounds having Formula I (below).

Also provided are processes for preparing compounds of Formula I.

The novel compounds of the present invention are potent inhibitors of proteases, especially trypsin-like serine proteases, such as chymotrypsin, trypsin, thrombin, plasmin and factor Xa. Certain of the compounds exhibit indirect antithrombotic activity via selective inhibition of factor Xa, or are intermediates useful for forming compounds having antithrombotic activity. Also provided are methods of inhibiting or treating aberrant proteolysis in a mammal and methods of treating thrombosis, ischemia, stroke, restenosis or inflammation in a mammal by administering an effective amount of a compound of Formula I.

The invention includes a composition for treating thrombosis, ischemia, stroke, restenosis or inflammation comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

DETAILED DESCRIPTION OF THE PREFERRED EMBODIMENTS

A first aspect of the invention is novel compounds of Formula I:

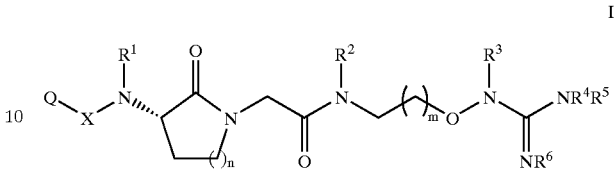

I or pharmaceutically acceptable salts thereof; wherein

Q is $C_{6-14}$ aryl, $C_{6-14}$ ar($C_{1-4}$)alkyl, $C_{6-14}$ ar($C_{2-4}$)alkenyl, pyridyl, thienyl, indolyl, quinolinyl, benzothienyl, or imidazolyl; any of which can include one or more optional substituents independently selected from halo, trifluoromethyl, hydroxy, amino, nitro, cyano, $C_{1-3}$ alkoxy, $C_{1-3}$ alkyl, methylenedioxy, carboxyamino, $C_{1-4}$ alkoxycarbonylamino, $C_{6-10}$ aryloxycarbonylamino, $C_{7-11}$ aralkoxycarbonylamino, aminocarbonyl, mono- or di-($C_{1-4}$)alkylaminocarbonyl, acetamido, amidino, pyridyl, naphthyl, pyrimidinyl, alkenyl, mono- or di-($C_{1-4}$) alkylamino, or combinations thereof;

X is methylene, carbonyl, or sulfonyl;

$R^1$ is hydrogen or $C_{1-3}$ alkyl;

n is 1, 2 or 3;

m is 1–4, preferably 1 or 2;

$R^2$ is hydrogen or $C_{1-3}$ alkyl;

$R^3$ is hydrogen or $C_{1-3}$ alkyl; and $R^4$, $R^5$ and $R^6$ are independently hydrogen, hydroxy, $C_{1-6}$alkyl, $C_{1-4}$ alkoxy, cyano or —$CO_2R^w$, where $R^w$, in each instance, is preferably one of $C_{1-4}$alkyl, $C_{4-7}$cycloalkyl, benzyl, or $R^w$ is one of

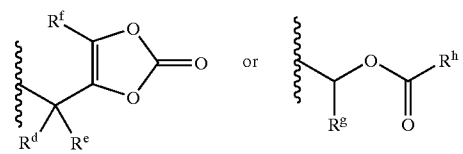

where $R^d$, $R^e$ and $R^g$ are each hydrogen, $R^f$ is methyl, and $R^h$ is benzyl or tert-butyl.

Preferred values of Q include aryl such as phenyl, biphenyl, or naphthyl; or aralkyl such as benzyl, phenethyl or naphthylmethyl; or thienyl. Any of these groups can be optionally substituted as defined above.

Suitable values include naphth-1-yl, naphth-2-yl, 5-dimethylaminonaphthlyl, 6-chloronaphth2yl, 6-bromonaphth-2-yl, benzyl, 2-nitrobenzyl, phenyl, 2-methylphenyl, 3-methylphenyl, 4-(n-propyl)phenyl, 4-(t-butyl)phenyl, 4-(t-amyl)phenyl, 4-methoxyphenyl, 4-iodophenyl, 4-fluorophenyl, 4-chlorophenyl, 3,4-dichlorophenyl, 4-nitrophenyl, 4-methylphenyl, 4-ethylphenyl, 4-ethenylphenyl, 3,4-dimethoxyphenyl, and 2-phenylethenyl.

Additional suitable values include 4-(2-methylphenyl) phenyl, 4-(2-methoxyphenyl)phenyl, 4-(3-chlorophenyl) phenyl, 4-(3-fluorophenyl)phenyl, 4-(3-methoxyphenyl) phenyl, 4-(4-fluorophenyl)phenyl, 4-(4-methylphenyl) phenyl, 4-(4-methoxyphenyl)phenyl, 4-(2,4-difluorophenyl) phenyl, 4-(3,4-dichlorophenyl)phenyl, 4-(3,4-dimethoxyphenyl)phenyl, 4-naphth-2-ylphenyl, 4-pyrid-4-ylphenyl, 4-pyrid-2-ylphenyl, biphenyl {(4-phenyl)phenyl}, 4-(4-chloro phenyl)phenyl, 4-pyrimidin-5-ylphenyl, and 5-(pyrid-5-yl)thien-2-yl.

Preferred values of n are 1 and 2.

Preferred values of X are $SO_2$ or C(O), most preferably $SO_2$.

Preferred values of m include 1 or 2, most preferably 1.

Suitable values for $R^1$, $R^2$, and $R^3$ include hydrogen, methyl, ethyl, n-propyl and isopropyl. Most preferably, each of $R^1$, $R^2$, and $R^3$ is hydrogen.

Suitable values of $R^4$, $R^5$ and $R^6$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$. In the most preferred embodiments, $R^4$, $R^5$ and $R^6$ are each hydrogen.

A preferred sub-genus of compounds of the present invention are those of Formula I wherein:

Q is phenyl, biphenylyl, naphthyl benzyl, phenethyl, naphthylmethyl, or thienyl, more preferably phenyl or biphenyl, any of these groups being optionally substituted by one to three optional substituents independently selected from halo, trifluoromethyl, hydroxy, amino, nitro, cyano, $C_{1-3}$ alkoxy, $C_{1-3}$ alkyl, methylenedioxy, carboxyamino, $C_{1-4}$ alkoxycarbonylamino, $C_{6-10}$ aryloxycarbonylamino, $C_{7-11}$aralkoxycarbonylamino, aminocarbonyl, mono- or di-($C_{1-4}$)alkylaminocarbonyl, acetamido, amidino, pyridyl, naphthyl, pyrimidinyl, alkenyl, mono- or di-($C_{1-4}$) alkylamino;

X is carbonyl, or sulfonyl, more preferably sulfonyl;

n is 1 or 2;

m is 1 or 2, more preferably 1;

$R^1$, $R^2$ and $R^3$ are hydrogen; and $R^4$, $R^5$ and $R^6$ are independently hydrogen, hydroxy, $C_{1-6}$alkyl, $C_{1-6}$alkoxy, cyano or —$CO_2R^w$, where $R^w$, in each instance, is preferably one of $C_{1-4}$alkyl, $C_{4-7}$cycloalkyl, benzyl, or $R^w$ is one of

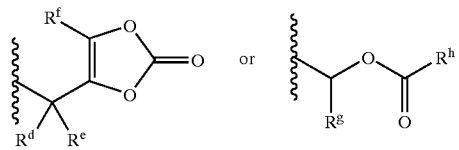

where $R^d$, $R^e$ and $R^g$ are each hydrogen, $R^f$ is methyl, and $R^h$ is benzyl or tert-butyl.

Compounds within the scope of the invention are described in the Examples.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The compounds of Formula I may also be solvated, especially hydrated. Hydration may occur during manufacturing of the compounds or compositions comprising the compounds, or the hydration may occur over time due to the hygroscopic nature of the compounds.

Certain compounds within the scope of Formula I are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process. Useful prodrugs are those where $R^4$, $R^5$ and/or $R^6$ are —$O_2R^w$, where $R^w$ is defined above.

When any variable occurs more than one time in any constituent or in Formula I, its definition on each occurrence is independent of its definition at every other occurrence.

Also, combinations of substituents and/or variables are permissible only if such combinations result in stable compounds.

The term "alkyl" as employed herein by itself or as part of another group refers to both straight and branched chain radicals of up to 10 carbons, unless the chain length is limited thereto, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, or decyl.

The term "alkenyl" is used herein to mean a straight or branched chain radical of 2–10 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 8 carbon atoms in length most preferably from 2 to 4 carbon atoms in length.

The term "alkynyl" is used herein to mean a straight or branched chain radical of 2–10 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The terms "alkoxy" refers to any of the above alkyl groups linked to an oxygen atom.

The term "aryl" as employed herein by itself or as part of another group refers to monocyclic or bicyclic aromatic groups containing from 6 to 12 carbons in the ring portion, preferably 6–10 carbons in the ring portion, such as phenyl, biphenyl, naphthyl or tetrahydronaphthyl.

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "halogen" or "halo" as employed herein by itself or as part of another group refers to chlorine, bromine, fluorine or iodine with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound, form a saturated or unsaturated 5-, 6-, or 7-membered ring.

The abbreviation "t-Am" used herein refers to an active amyl moiety having the structure $CH_3CH_2(CH_3)_2C-$.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Preferred acids for forming acid addition salts include HCl, acetic acid, trifluoroacetic acid and fumaic acid.

A second aspect of the present invention is directed to a method of treating thrombosis, ischemia, stroke, restenosis or inflammation comprising administering to a mammal in need of said treatment a therapeutically or prophylactically effective amount of a compound of Formula I.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention.

The compounds of the present invention are preferably employed to inhibit trypsin-like proteases.

The compounds of the present invention are distinguished by their ability to preferentially inhibit factor Xa in comparison to thrombin and/or plasmin. As factor Xa inhibitors, the compounds of the present invention inhibit thrombin production. Therefore, the compounds are useful for the treatment or prophylaxis of states characterized by abnormal venous or arterial thrombosis involving either thrombin production or action. These states include, but are not limited to: deep vein thrombosis; disseminated intravascular coagulopathy that occurs during septic shock, viral infections, and cancer; myocardial infarction; stroke; coronary artery bypass; hip replacement; and thrombus formation resulting from either thrombolytic therapy or percutaneous transluminal coronary angioplasty (PCTA). The compounds of the present invention may also be used as an anticoagulant in extracorporeal blood circuits. By virtue of the effects of both factor Xa and thrombin on a host of cell types, such as smooth muscle cells, endothelial cells and neutrophils, the compounds of the present invention find additional use in the treatment or prophylaxis of adult respiratory distress syndrome; inflammatory responses, such as edema; reperfusion damage; atherosclerosis; and restenosis following an injury such as balloon angioplasty, atherectomy, and arterial stent placement.

The compounds of the present invention may be useful in treating neoplasia and metastasis, as well as neurodegenerative diseases, such as Alzheimer's disease and Parkinson's disease.

The compounds of the present invention may be used in combination with thrombolytic agents, such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

Compounds of the present invention that arc distinguished by their ability to inhibit thrombin may be employed for a number of therapeutic purposes. As thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA). Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, and blood lines. The compounds of the present invention may also be used as an anticoagulant in extracorporeal blood circuits.

By virtue of the effects of thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement.

The compounds of the present invention may be useful in treating neoplasia and metastasis as well as neurodegenerative diseases, such as Alzheimer's disease and Parkinson's disease.

When employed as factor Xa inhibitors, the compounds of the present invention may be administered in an effective amount within the dosage range of about 0.1 to about 500 mg/kg, preferably between 0.1 to 10 mg/kg body weight, on a regimen in single or 2–4 divided daily doses.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The present invention is also directed to methods of making compounds of Formula I, comprising:

coupling or condensing a compound of Formula II:

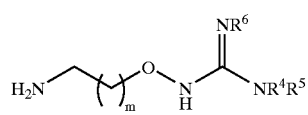

II or a salt thereof, where $R^4$, $R^5$ and $R^6$ are as defined herein or optionally protected, and m is as defined herein, with a compound of Formula III:

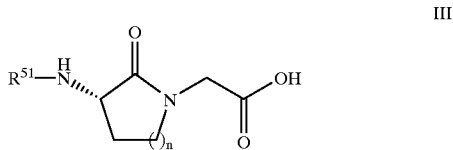

III where $R^{51}$ is H or Q-X—, where Q, X, $R^1$, $R^2$, $R^3$, $R^4$, $R^5$, and $R^6$ are as defined herein. In general, $R^4$, $R^5$, and $R^6$ groups may either be hydrogen or an amino protecting group.

Compounds of the present invention can be synthesized according to the following schemes.

Reagents and starting materials used in the following methods are commercially available from chemical vendors, including Aldrich, Advanced ChemTech, Bachem, Sigma, Fluka, and the like. During the synthesis of these compounds, functional groups are protected by blocking groups to prevent cross reaction. Examples of suitable blocking groups and their use are described in Greene, T. W.

and Wuts, P. G. M., *Protective Groups in Organic Synthesis*, second edition, John Wiley & Sons, New York, N.Y. (1991). Blocking groups are also referred to herein as protective groups.

Scheme 1 details the synthetic steps to produce aminoalkoxyguanidine starting materials of Formula II. The variable "m" in the schemes has a value of from 1 to 8, preferably 1 or 2. The synthetic steps in this scheme are described in further detail and exemplified in Examples 1 and 2 of commonly assigned published PCT application WO99/26926, published Jun. 3, 1999.

Scheme 1

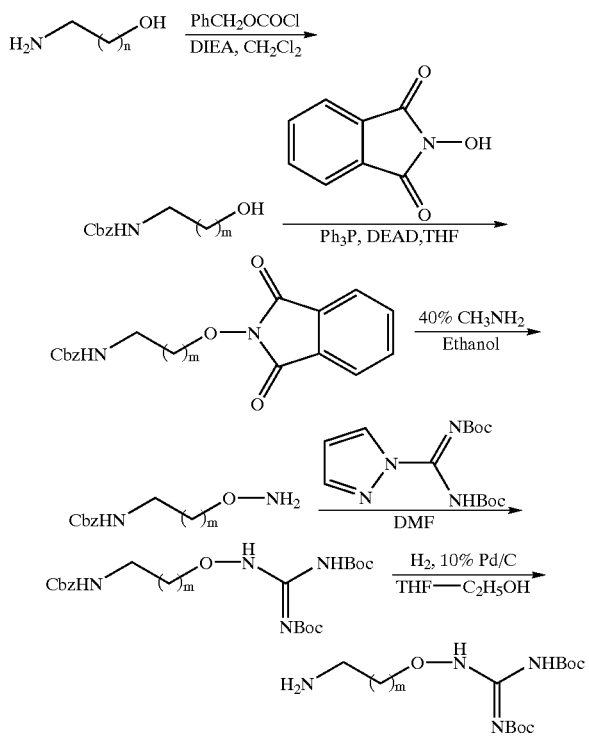

Preparation of the γ- and δ-lactam starting materials III having a carboxymethyl group at the 1-position and an amino group possessing a suitable protective group $P^b$ at the 3-position have been described previously by Freidinger et al., *J. Org. Chem.* 47:104–109(1982). The analogous 7-membered ring lactam has also been described (Semple, J. E. et al., *J. Med. Chem.* 39:4531–4536 (1996). Alternatively, the δ-lactam can be synthesized by cyclization of ornithine with a suitable protective group on the α-amino group using an amide coupling reagent such as 1-ethyl-3-(3-dimethylaminopropyl)carbodiimide hydrochloride. The carboxymethyl group can then be installed by alkylation with an α-bromoacetic acid ester using a base such as lithium bis(trimethylsilyl)amide in a solvent such as tetrahydrofuran or N,N-dimethylformamide, followed by saponification with aqueous methanolic hydroxide. The analogous γ-lactam can also be synthesized by a modified Curtius-type rearrangement at the γ-carboxyl group of glutamic acid having suitable protective groups on the α-amino and α-carboxy groups similar to that described by Scholtz and Bartlett, *Synthesis:*542–544 (1989). Spontaneous cyclization is then effected by removal of the resulting γ-amino protective group and conversion to the free base (if necessary). Introduction of the carboxymethyl side chain can then be carried out as previously described.

Scheme 2

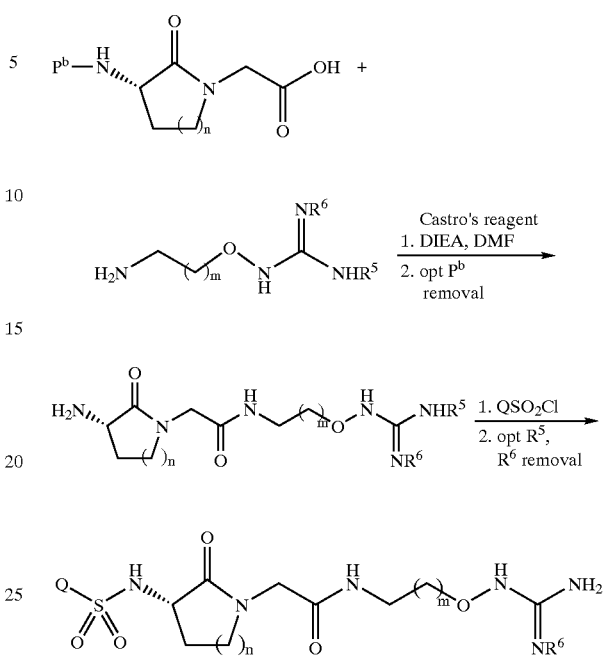

Scheme 2 illustrates the coupling of the synthesis of compounds of the invention starting with the coupling of starting materials of Formulae II and III. The starting materials can be coupled using standard coupling agents such as N,N'-dicyclohexylcarbodiimide and other well-known agents described in *The Peptides: Analysis, Synthesis, Biology*, Gras, E. et al., eds., Academic Press, New York, N.Y. (1979–1987), Volumes 1 to 8. The protective group $P^b$ can then be removed using conditions described in Greene, T. W. and Wuts, P. G. M., *Protective Groups in Organic Synthesis*, second edition, John Wiley & Sons, New York, N.Y. (1991). The resulting amine can then be acylated with a sulfonyl chloride in an inert solvent, such as methylene chloride, preferably in the presence of an organic base such as pyridine, triethylamine, and the like. Removal of protective groups $R^5$ and $R^6$ can be accomplished using the methods described in Greene, T. W. and Wuts, P. G. M., *Protective Groups in Organic Synthesis*, second edition, John Wiley & Sons, New York, N.Y. (1991) to provide the final compound.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

2-{(3S)-3-[(2-Naphthylsulfonyl)amino]-2-oxopiperidyl}-N-[2-(amidinoaminooxy)ethyl] acetamide

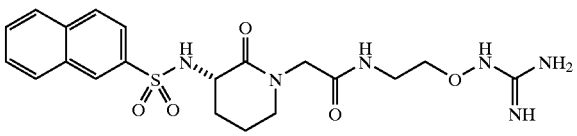

1. N-((3S)-2-Oxo(3-piperidyl))(phenylmethoxy)carboxamide

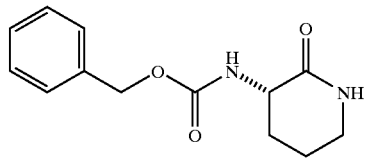

1-(3-Dimethylaminopropyl)-3-ethylcarbodiimide hydrochloride (7.2 g, 37.6 mmol) was added in a single portion to a solution of N^α-benzyloxycarbonyl-L-ornithine (10 g, 37.6 mmol), 4-methylmorpholine (4.1 mL, 37.6 mmol), and 1-hydroxybenzotriazole (5.1 g, 37.6 mmol) in acetonitrile (200 mL). After being stirred overnight, the undissolved white solid was filtered off and discarded. The filtrate was concentrated in vacuo and the residue was dissolved in methylene chloride and washed sequentially with dilute aqueous HCl and dilute aqueous NaHCO₃. The separated organic layer was dried (MgSO₄), filtered, and concentrated in vacuo to give a white solid (7.0 g, 75%). $^1$H-NMR (300 Mz, CDCl₃) δ 7.34 (m, 5H), 6.20 (bs, 1H), 5.76 (bs, 1H), 5.11 (s, 2H), 4.10 (m, 1H), 3.32 (m, 1H), 2.50 (m, 1H), 1.92 (m, 2H), 1.61 (m, 1H).

2. 2-{(3S)-2-Oxo-3-[(phenylmethoxy)carbonylamino]pipetidyl}acetic Acid

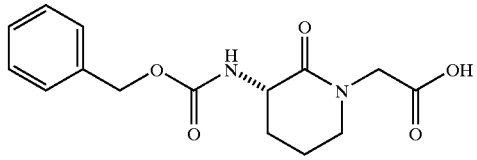

Lithium bis(trimethylsilyl)amide (20.8 mL, 1.0 M in tetrahydrofuran) was dropped into an ice-cooled solution of the product from the preceding experimental (4.7 g, 18.9 mmol) in tetrahydrofuran (20 mL). Upon complete addition, ethyl bromoacetate (15.8 g, 94.5 mmol) was dropped into the mixture. After being stirred for 30 minutes, ethylenediamine (10 mL) was added and stirring was continued for an additional 30 minutes. The mixture was concentrated in vacuo and the residue was dissolved in methylene chloride and washed with dilute aqueous HCl. The separated organic layer was dried (Na₂SO₄), filtered, and concentrated in vacuo. The crude product was dissolved in methanol (25 mL) followed by the addition of 1.0 M NaOH (50 mL). After being stirred for 30 minutes, the methanol was evaporated in vacuo and the resulting basic aqueous solution was extracted with methylene chloride (3×100 mL). The aqueous layer was then acidified with 1.0 N HCl to a pH of 1 and extracted with methylene chloride. The organic extracts were dried (Na₂SO₄), filtered, and concentrated in vacuo to give the title compound (5.7 g, 98%). No further purification was necessary.

3. tert-Butyl-3-{[2-(2-{(3S)-2-oxo-3-[(phenylmethoxy)carbonylamino]piperidyl}acetylamino)ethoxy]-amino}-2-aza-3-[(tert-butoxy)carbonylamino]prop-2-enoate

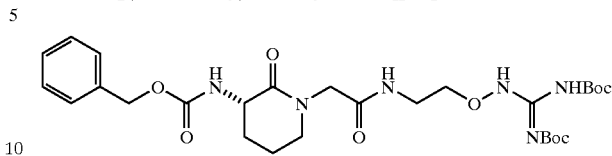

Benzotriazol-1-yloxytris(dimethylamino)phosphonium hexafluorophosphate, 5.25 g, 12 mmol) was added in a single portion to a solution of the product from the preceding experimental (3.0 , 9.9 mmol), tert-butyl 3-[(2-aminoethoxy)amino]-2-aza-3-[(tert-butoxy)carbonylamino]prop-2-enoate (3.5 g, 9.9 mmol), and N,N-diisopropylethylamine (3.45 mL, 19.8 mmol) in N,N-dimethylformamide (40 mL). After being stirred overnight, the mixture was diluted with methylene chloride and washed sequentially with dilute aqueous HCl and dilute aqueous NaHCO₃. The separated organic layer was dried (Na₂SO₄), filtered, and concentrated in vacuo to give the title compound as impure material (7.0 g) which was used crude in the next step.

4. tert-Butyl-3-({2-[2-((3S)-3-amino-2-oxopiperidyl)acetylamino] ethloxy}amino)-2-aza-3-[(tert-butoxy)carbonylamino]prop-2-enoate

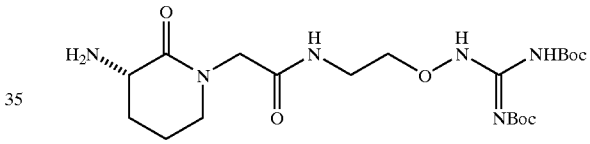

A solution of the crude product from the preceding experimental (7.0 g) and 10% palladium on carbon (800 mg) in methanol (100 mL) was stirred under 1 atmosphere of hydrogen for 2 hours. The mixture was filtered through diatomaceous earth and the filtrate was concentrated in vacuo. The residue was partitioned between methylene chloride and dilute aqueous HCl. The aqueous phase was extracted two more times with methylene chloride and these extracts were discarded. The aqueous layer was basified with 1 M NaOH and extracted with methylene chloride. The separated organic extracts were dried (Na₂SO₄), filtered, and concentrated in vacuo to give the title compound (2.0 g, 40% for steps 3 and 4) for which further purification was not necessary.

5. 2-{(3S)-3-[(2-Naphthylsulfonyl)amino]-2-oxopiperidyl}-N-[2-(amidinoaminooxy)ethyl]acetamide

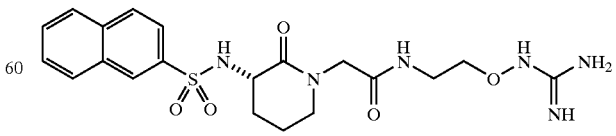

2-Naphthalenesulfonyl chloride (48 mg, 0.21 mmol) was added in a single portion to a solution of the product from the preceding experimental (100 mg, 0.21 mmol) and dimethylaminopyridine on polystyrene (250 mg, ≈2 mmol dimethylaminopyridine/g resin) in methylene chloride (3 mL). After being stirred overnight, the mixture was diluted with acetonitrile (3 mL) followed by the addition of aminomethyl resin (250 mg, ≈1.1 mmol/g resin). After being stirred for 30 minutes, the resins were removed by filtration and the filtrate was concentrated in vacuo. The residue was dissolved in methylene chloride (2 mL) and trifluoroacetic acid (2 mL), and stirred for 30 minutes. The mixture was then concentrated in vacuo and chromatographed on a 10 g silica SPE column using 10% methanol/methylene chloride saturated with ammonia. After concentrating the desired fractions, the product was stirred in methanol with 1 equivalent of fumaric acid, and concentrated in vacuo to give the title compound as a white solid (32 mg, 26%). MS: m/z= 463(M+1).

The tert-butyl 3-[(2-aminoethoxy)amino]-2-aza-3-[(tert-butoxy)carbonylamino]prop-2-enoate was prepared as follows:

a. N-(2-Hydroxyethyl)(phenylmethoxy)carboxamide

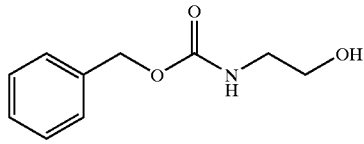

Benzyl chloroformate (63 mL, 443 mmol) was added dropwise to a solution of ethanolamine (60 g, 984 mmol) in tetrahydrofuran (300 mL). After being stirred overnight, the mixture was concentrated in vacuo, and partitioned between methylene chloride and dilute aqueous HCl. The separated organic layer was washed with dilute aqueous $NaHCO_3$, dried ($MgSO_4$), filtered, and concentrated in vacuo to give the title compound (36 g) which was used without further purification in the next step.

b. N-[2-(1,3-Dioxoisoindolin-2-yloxy)ethyl](phenylmethoxy) carboxamide

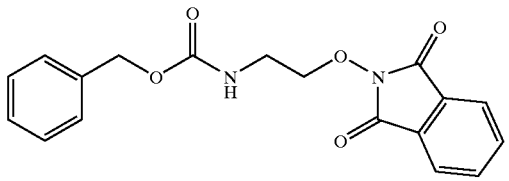

Diethyl azodicarboxylate (5.2 g, 30 mmol) was added to a solution of the product from the preceding experimental (5.9 g, 30 mmol), N-hydroxyphthalimide (4.9 g, 30 mmol), and triphenylphosphine (7.9 g, 30 mmol) in tetrahydrofuran (100 mL). After being stirred overnight, the mixture was diluted with ethyl acetate (200 mL), and washed with saturated aqueous $NaHCO_3$ (2×100 mL) and brine (100 mL). The separated organic layer was dried ($Na_2SO_4$), filtered, and concentrated in vacuo. The residue was chromatographed ($SiO_2$) using a gradient elution with 0–4% ethyl acetate in methylene chloride to give the title compound as a white solid (9.3 g, 91%). $^1$H-NMR (300 MHz, $CDCl_3$) δ 7.84 (m, 2H), 7.78 (m, 2H), 7.37 (m, 5H), 5.97 (bs, 1H), 5.14 (s, 2H), 4.27 (t, J=4.9 Hz, 2H), 3.51 (q, J=5.2 Hz, 2H).

c. N-[2-(aminooxy)ethyl](phenylmethoxy)carboxamide

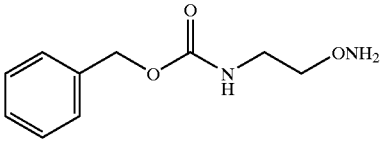

Methylamine (40% wt. solution in $H_2O$, 2 mL, 25 mmol) was added to a solution of the product from the preceding experimental (1.36 g, 4.0 mmol) in ethanol (20 mL) and tetrahydrofuran (20 mL). After being stirred for 1 hour, the mixture was concentrated in vacuo, and the resulting residue was chromatographed ($SiO_2$) using a gradient elution with 75–100% ethyl acetate in hexanes to give the title compound as a white solid (800 mg, 95%). $^1$H-NMR (300 MHz, $CDCl_3$) δ 7.36 (m, 5H), 5.47 (bs, 2H), 5.21 (bs, 1H), 5.10 (s, 2H), 3.72 (t, J=5.0 Hz, 2H), 3.44 (q, J=5.0 Hz, 2H).

d. tert-Butyl-2-aza-3-[(tert-butoxy)carbonylamino]-3-({2-[(phenylmethoxy)carbonylamino]ethoxy}amino)prop-2-enoate

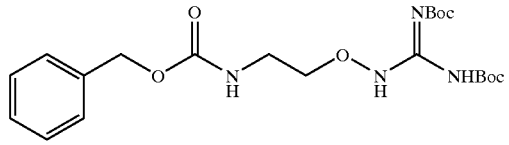

A solution of the product from the preceding experimental (780 mg, 3.7 mmol) and [N,N'-di(tert-butoxycarbonyl)]amidinopyrazole (1.25 g, 4.0 mmol) in N,N-dimethylformamide (20 mL) was stirred overnight. The mixture was concentrated under high vacuum, and the resulting residue was chromatographed ($SiO_2$) using a gradient elution with 0–5% ethyl acetate in methylene chloride to give the title compound as a colorless oil (1.55 g, 93%). $^1$H-NMR (300 MHz, $CDCl_3$) δ 9.08 (s, 1H), 7.67 (s, 1H), 7.33 (m, 5H), 6.21 (bs, 1H), 5.21 (bs, 1H), 5.11 (s,2H), 4.12 (t, J=4.8 Hz, 2H), 3.54 (q, J=4.9 Hz, 2H), 1.49 (s, 9H), 1.46 (s, 9H).

e. tert-Butyl-3-[(2-aminoethoxy)amino]-2-aza-3-[(tert-butoxy)carbonylamino]prop-2-enoate

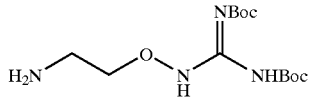

A solution of the product from the preceding experimental (730 mg, 1.5 mmol) and 10% Palladium on carbon (70 mg) in ethanol (20 mL) and tetrahydrofuran (20 mL) was stirred under 1 atmosphere of hydrogen for 30 min. The mixture was filtered through diatomaceous earth, and the filtrate was concentrated in vacuo. The residue was chromatographed on a 10 g silica SPE column using 5% methanol/methylene chloride saturated with ammonia to give the title compound as a colorless oil (290 mg, 61%). $^1$H-NMR (300 MHz, $CDCl_3$) δ 9.08 (bs, 1H), 4.08 (t, J=5.2 Hz, 2H), 2.99 (q, J=5.1 Hz, 2H), 1.50 (s, 9H), 1.48 (s, 9H).

The compounds described in Table 1 below were synthesized in the same manner as Example 1. These compounds were all synthesized as fumarates.

TABLE 1
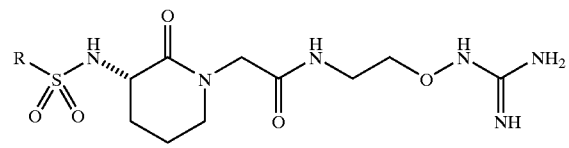
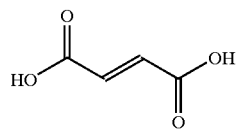
| Example No. | R | MS: m/z (M + 1) |
|---|---|---|
| 2 | 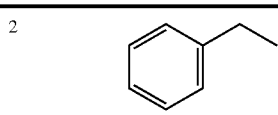 | 427 |
| 3 | 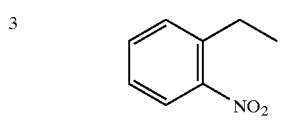 | 472 |
| 4 | 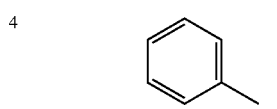 | 413 |
| 5 | 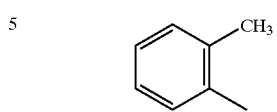 | 427 |
| 6 | 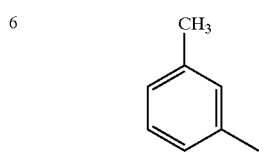 | 427 |
| 7 | 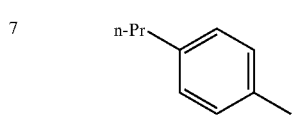 | 455 |
| 8 | 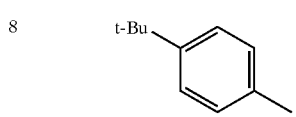 | 469 |
| 9 | 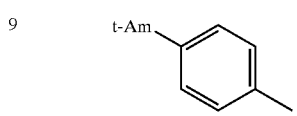 | 483 |
| 10 | 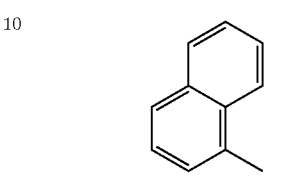 | 463 |
| 11 | 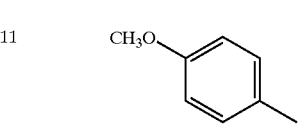 | 443 |
TABLE 1-continued
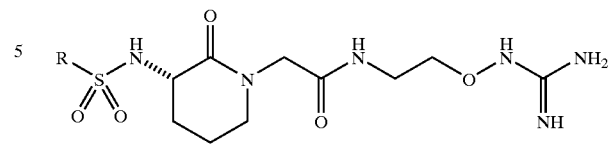
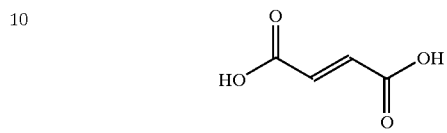
| Example No. | R | MS: m/z (M + 1) |
|---|---|---|
| 12 | 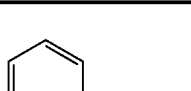 | 439 |
| 13 | 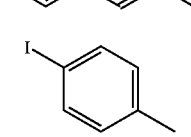 | 539 |
| 14 | 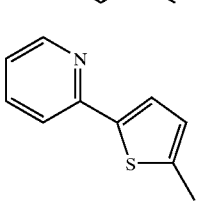 | 496 |
| 15 | 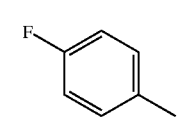 | 431 |
| 16 | 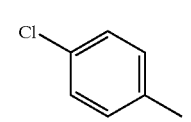 | 447 |
| 17 | 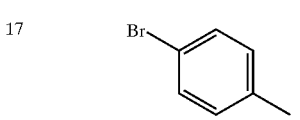 | 491/493 |
| 18 | 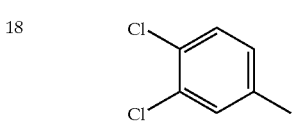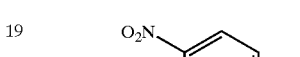 | 481/483 |
| 19 | 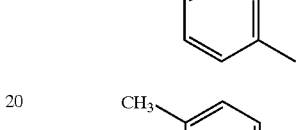 | 458 |
| 20 | 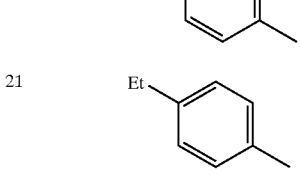 | 427 |
| 21 | | 441 |

TABLE 1-continued

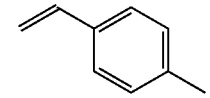

| Example No. | R | MS: m/z (M + 1) |
|---|---|---|
| 22 | 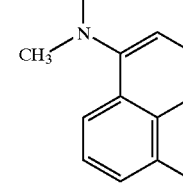 | 439 |
| 23 | 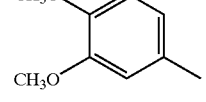 | 506 |
| 24 | 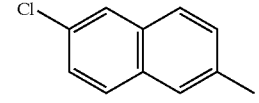 | 473 |
| 25 | 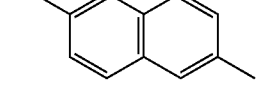 | 497 |
| 26 | 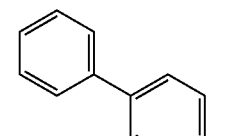 | 541/543 |
| 27 | 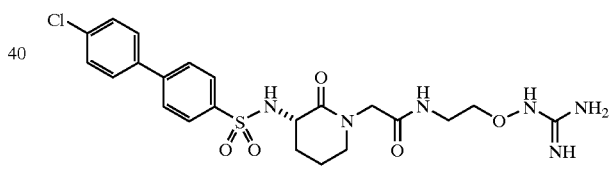 | 489 |

EXAMPLE 28

2-[(3S)-3-({[4-(4-Chlorophenyl)phenyl]sulfonyl}amino)-2-oxopiperidyl]-N-[2-(amidinoaminooxy)ethyl]acetamide 1. tert-Butyl-3-({2-[2-((3S)-3-{[[(4-iodophenyl)sulfonyl]amino}-2-oxopiperidyl)acetylamino]ethoxy}amino)-2-aza-3-[(tert-butoxy)carbonylamino]prop-2-enoate

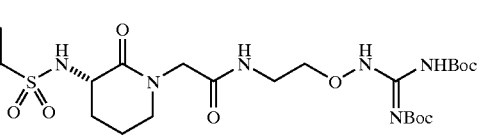

Pipsyl chloride (1.77 g, 5.8 mmol) was added to a solution of the product from Example 1.4 (2.50 g, 5.3 mmol) and triethylamine (0.89 mL, 6.4 mmol) in methylene chloride (20 mL). After being stirred overnight, the mixture was diluted with acetonitrile (20 mL) followed by the addition of aminomethyl resin (1 g, ≈1.1 mmol/g resin). The resin was filtered off and the filtrate was concentrated in vacuo to give the title compound (2.48 g, 87%) which was used without purification in the next step.

2. 2-[(3S)-3-({[4-(4-Chlorophenyl)phenyl]sulfonyl}amino)-2-oxopiperid yl]-N-[2-(amidinoaminooxy)ethyl]acetamide

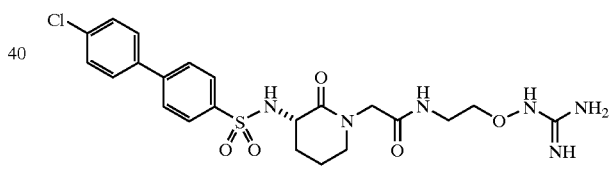

The product from the preceding experimental (100 mg, 0.14 mmol) was dissolved in toluene (1 mL) and added to a vial containing 4-chlorophenylboronic acid (31 mg, 0.2 mmol) and dichlorobis(triphenylphosphine)palladium(II) (10 mg). This mixture was then diluted with ethanol (0.25 mL) and saturated aqueous sodium bicarbonate (0.25 mL), capped, and heated in a sand bath at 80° C. until the color turned black (approximately 30 minutes). The mixture was directly applied to a 10 g silica SPE column and chromatographed using ethyl acetate as eluent. The desired fractions were concentrated in vacuo and the residue was dissolved in trifluoroacetic acid/methylene chloride (1:1, 4 mL). After being stirred for 30 minutes, the mixture was concentrated in vacuo and the residue was chromatographed on a 10 g silica SPE column using 10% methanol/methylene chloride saturated with ammonia. The desired fractions were concentrated and dissolved in methanol containing one equivalent of fumaric acid to give the title compound as a fumarate salt (15 mg, 17%). MS: m/z=523(M+1).

EXAMPLE 29

2-((3S)-2-Oxo-3-{[(4-pyrimidin-5-ylphenyl)sulfonyl]amino}piperidyl)-N-[2-(amidinoaminooxy)ethyl]acetamide

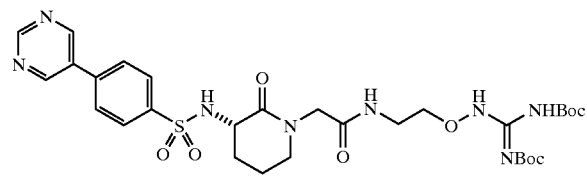

The product from Example 29.1 (100 mg, 0.14 mmol), lithium chloride (25 mg, 0.60 mmol), copper(I) iodide (3 mg), dichlorobis(triphenylphosphine) palladium(II) (7 mg), and 5-tributylstannylpyrimidine were combined in a vial, dissolved/suspended in toluene (1 mL), capped, and heated in a sand bath at 80° C. until the color turned black (approximately 30 minutes). The mixture was directly applied to a 10 g silica SPE column and chromatographed using ethyl acetate as eluent. The desired fractions were concentrated in vacuo and the residue was dissolved in trifluoroacetic acid/methylene chloride (1:1, 4 mL). After being stirred for 30 minutes, the mixture was concentrated in vacuo and the residue was chromatographed on a 10 g silica SPE column using 10% methanol/methylene chloride saturated with ammonia. The desired fractions were concentrated and dissolved in methanol containing one equivalent of fumaric acid to give the title compound as a fumarate salt (13 mg, 15%). MS: m/z=491(M+1).

The compounds described in Table 2 below were synthesized in the same manner as Example 28, except for Example 44 which was synthesized in the same manner as Example 29. These compounds were all synthesized as fumarates.

TABLE 2

| Example No. | Ar | MS: m/z (M + 1) |
|---|---|---|
| 30 | 2-CH₃-phenyl | 503 |
| 31 | 2-OCH₃-phenyl | 519 |
| 32 | 3-F-phenyl | 507 |
| 33 | 3-Cl-phenyl | 523 |
| 34 | 3-CH₃-phenyl | 503 |
| 35 | 3-CH₃O-phenyl | 519 |
| 36 | 4-F-phenyl | 507 |
| 37 | 4-CH₃-phenyl | 503 |
| 38 | 4-CH₃O-phenyl | 519 |
| 39 | 2,4-diF-phenyl | 525 |
| 40 | 2,3-diCl-phenyl | 557/559 |
| 41 | 3,4-di(CH₃O)-phenyl | 549 |

TABLE 2-continued

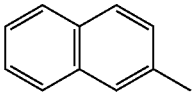

| Example No. | Ar | MS: m/z (M + 1) |
|---|---|---|
| 42 | 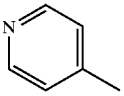 | 539 |
| 43 | 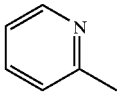 | 490 |
| 44 | 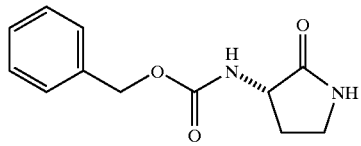 | 490 |

EXAMPLE 45

2-((3S)-3-{[(6-Bromo(2-naphthyl))sulfonyl]amino}-
2-oxopyrrolidinyl)-N-[2-(amidinoaminooxy)ethyl]
acetamide

1. N-((3S)-2-Oxopyrrolidin-3-yl)(phenylmethoxy) carboxamide

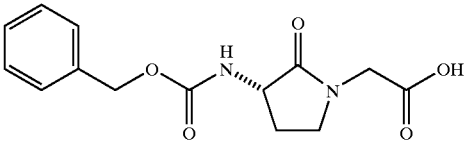

Diphenylphosphoryl azide (11.1 mL, 51.3 mmol) was dropped into a solution of N-benzyloxycarbonyl-L-glutamic acid α-methyl ester (13.8 g, 46.7 mmol) and triethylamine (7.2 mL, 51.3 mmol) in tert-butanol. After being stirred overnight at 95° C., the mixture was concentrated in vacuo, dissolved in methylene chloride, and washed sequentially with dilute aqueous HCl and dilute aqueous NaHCO$_3$. The separated organic layer was dried (MgSO$_4$), filtered, and concentrated in vacuo. The addition of diethyl ether resulted in the formation of a precipitate which was filtered off to give phenylmethyl (6S)-6-(methoxycarbonyl)-2-oxo-1,3-diazaperhydroinecarboxylate as a white solid (4.0 g, 29%). $^1$H-NMR (300 MHz, DMSO-d$_6$) δ 7.37 (m, 6H), 5.18 (s, 2H), 4.83 (t, J=5.2 Hz, 1H), 3.65 (s, 3H), 3.10 (m, 1H), 2.95 (m, 1H), 2.16 (m, 1H), 2.03 (m, 1H). The filtrate was concentrated in vacuo and the residue was dissolved in methylene chloride (50 mL) followed by the addition of trifluoroacetic acid (50 mL). After being stirred for 30 minutes, the mixture was concentrated in vacuo and the residue was partitioned between methylene chloride and dilute aqueous sodium hydroxide. The separated organic layer was dried (MgSO$_4$), filtered, and concentrated in vacuo. The addition of diethyl ether resulted in the formation of a precipitate which was filtered off to give the title compound as a white solid (3.0 g, 28%). $^1$H-NMR (300 MHz, DMSO-d$_6$) δ 7.78 (bs, 1H), 7.51 (d, J=8.8 Hz, 1H), 7.36 (m, 5H), 5.03 (s, 2H), 4.09 (m, 1H), 3.14 (m, 2H), 2.26 (m, 1H), 1.85 (m, 1H).

2. 2-{(3S)-2-Oxo-3-[(phenylmethoxy)carbonylamino]pyrrolidinyl}acetic Acid

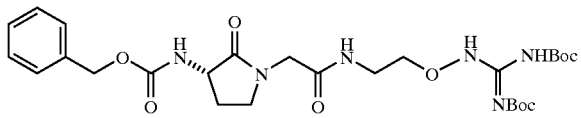

Lithium bis(trimethylsilyl)amide (13 mL, 1.0 M in tetrahydrofuran) was dropped into an ice-cooled solution of the product from the preceding experimental (2.77 g, 11.8 mmol) in tetrahydrofuran (60 mL). Upon complete addition, ethyl bromoacetate (2.6 mL, 23.7 mmol) was dropped into the mixture. After being stirred for 30 minutes, ethylenediamine (1.2 mL) was added and stirring was continued for an additional 30 minutes. The mixture was concentrated in vacuo, the residue was dissolved in methylene chloride, and washed sequentially with dilute aqueous HCl and dilute aqueous NaHCO$_3$. The separated organic layer was dried (MgSO$_4$), filtered, and concentrated in vacuo. The crude product (3.5 g) was dissolved in methanol (60 mL) followed by the addition of 1.0 M NaOH (40 mL). After being stirred overnight, the methanol was evaporated in vacuo and the resulting basic aqueous solution was extracted twice with methylene chloride (discarded). The aqueous layer was then acidified with 1.0 N HCl to a pH of 1–2 and extracted with methylene chloride. The aqueous layer was then saturated with sodium chloride (solid), and further extracted with ethyl acetate. The combined organic extracts were dried (Na$_2$SO$_4$), filtered, and concentrated in vacuo. The addition of diethyl ether resulted in the formation of a precipitate which was filtered to give the title compound as a white solid (3.0 g, 86%). No further purification was necessary.

3. tert-Butyl-3-{[2-(2-{(3S)-2-oxo-3-[(phenylmethoxy)carbonylamino]pyrrolidinyl}acetylamino)ethoxy]amino}-2-aza-3-[(tert-butoxy)carbonylamino]prop-2-enoate Benzotriazol-1-yloxytris(dimethylamino)phosphonium hexafluorophosphate (4.8 g, 10.8 mmol) was added in a single portion to a solution of the product from the preceding experimental (2.9 g, 9.8 mmol), tert-butyl 3-[(2-aminoethoxy)amino]-2-aza-3-[(tert-butoxy)carbonylamino] prop-2-enoate (3.4 g, 10.8 mmol), and N,N-diisopropylethylamine (1.9 mL, 10.8 mmol) in N,N-dimethylformamide (80 mL). After being stirred overnight, the mixture was concentrated in vacuo, diluted up with methylene chloride, and washed sequentially with dilute aqueous HCl and dilute aqueous NaHCO₃. The separated organic layer was dried (MgSO₄), filtered, and concentrated in vacuo to give the title compound as a crude product (7.5 g) which was used without purification in the next step.

4. tert-Butyl 3-({2-[2-((3S)-3-amino-2-oxopyrrolidinyl)acetylamino]ethoxy}amino)-2-aza-3-[(tert-butoxy)carbonylamino]prop-2-enoate

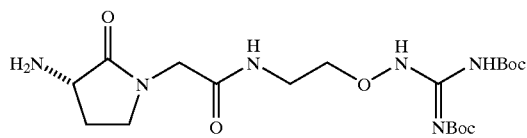

A solution of the product from the preceding experimental (7.5 g crude) and 10% palladium on carbon (750 mg) in ethanol (100 mL) and chloroform (7 mL) was stirred overnight under 1 atmosphere of hydrogen. The mixture was filtered through diatomaceous earth, and the filtrate was concentrated in vacuo. The residue was partitioned between methylene chloride and 0.1 N HCl. The aqueous layer was extracted a second time with methylene chloride and these extracts were discarded. The aqueous layer was then basified with 1.0 M NaOH to a pH of 10–11, and extracted with methylene chloride. The separated organic layer was dried (Na₂SO₄), filtered, and concentrated in vacuo to give the title compound as a colorless oil (1.0 g, 22% for steps 3 and 4). No further purification was necessary.

5. 2-{(3S)-3-([(6-Bromo(2-naphthyl))sulfonyl]amino}-2-oxopyrrolidinyl)-N-[2-(amidinoaminooxy)ethyl]acetamide

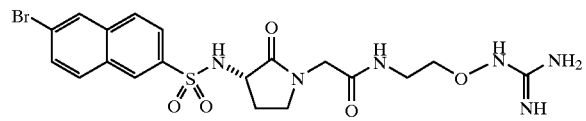

6-Bromo-2-naphthalenesulfonyl chloride (73 mg, 0.24 mmol) was added in a single portion to a solution of the product from the preceding experimental (100 mg, 0.21 mmol) and dimethylaminopyridine on polystyrene (220 mg, ≈2 mmol dimethylaminopyridine/g resin) in methylene chloride (3 mL). After being stirred overnight, the mixture was diluted with acetonitrile (3 mL) followed by the addition of aminomethyl resin (250 mg, ≈1.1 mmol/g resin). After being stirred for 30 minutes, the resins were removed by filtration and the filtrate was concentrated in vacuo. The residue was dissolved in methylene chloride (2 mL) and trifluoroacetic acid (1 mL), and stirred for 30 minutes. The mixture was then concentrated in vacuo and chromatographed on a 10 g silica SPE column using 10% methanol/methylene chloride saturated with ammonia. After concentrating the desired fractions, the product was stirred in methanol with 1 equivalent of fumaric acid, and concentrated in vacuo to give the title compound as a white solid (64 mg, 42%). MS: m/z=527/529(M+1).

The compounds described in Table 3 below were synthesized in the same manner as Example 28, except that the compound from Example 45.4 was used as starting material. These compounds were all synthesized as fumarates.

TABLE 3

| Example No. | Ar | MS: m/z (M + 1) |
|---|---|---|
| 46 | 3-Cl-phenyl | 509 |
| 47 | 3-CH₃O-phenyl | 505 |
| 48 | 4-F-phenyl | 493 |
| 49 | 4-Cl-phenyl | 509 |
| 50 | 4-CH₃O-phenyl | 505 |

EXAMPLE 51

Tablet Preparation

Tablets containing 25.0, 50.0, and 100.0 mg, respectively, of the following active compounds are prepared as illustrated below:

a. 2-{(3S)-3-[(2-Naphthylsulfonyl)amino]-2-oxopiperidyl}-N-[2-(amidinoaminooxy)ethyl]acetamide; and b. 2-((3S)-3-{[(6-Bromo(2-naphthyl))sulfonyl]amino}-2-oxopyrrolidinyl)-N-[2-(amidinoaminooxy)ethyl]acetamide.

| TABLET FOR DOSES CONTAINING FROM 25–100 MG OF THE ACTIVE COMPOUND | | | |
|---|---|---|---|
| | Amount-mg | | |
| Active Compound | 25.0 | 50.0 | 100.00 |
| Microcrystalline cellulose | 37.25 | 100.0 | 200.00 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 52

Intravenous Solution Preparation

An intravenous dosage form of the above-indicated active compounds is prepared as follows:

| Active Compound | 0.5–10.0 mg |
| --- | --- |
| Sodium Citrate | 5–50 mg |
| Citric Acid | 1–15 mg |
| Sodium Chloride | 1–8 mg |
| Water for Injection (USP) | q.s. to 1 ml |

Utilizing the above quantities, the active compound 2-{(3S)-3-[(2-Naphthylsulfonyl)amino]-2-oxopiperidyl}-N-[2-(amidinoaminooxy)ethyl]acetamide is dissolved at room temperature in a previously prepared solution of sodium chloride, citric acid, and sodium citrate in Water for Injection (USP, see page 1636 of United States Pharmacopeia/National Formulary for 1995, published by United States Pharmacopcial Convention, Inc., Rockville, Md. (1994).

EXAMPLE 53

In vitro Inhibition of Purified Enzymes

Reagents: All buffer salts were obtained from Sigma Chemical Company (St. Louis, Mo.), and were of the highest purity available. The enzyme substrates, N-benzoyl-Phe-Val-Arg-p-nitroanilide (Sigma B7632), N-benzoyl-Ile-Glu-Gly-Arg-p-nitroanilide hydrochloride (Sigma B2291), N-p-Tosyl-Gly-Pro-Lys-p-nitroanilide (Sigma T6140), N-succinyl-Ala-Ala-Pro-Phe-p-nitroanilide (Sigma S7388) and N-CBZ-Val-Gly-Arg-p-nitroanilide (Sigma C7271) were obtained from Sigma. N-succinyl-Ala-Ala-Pro-Arg-p-nitroanilide (BACHEM L-1720) and N-succinyl-Ala-Ala-Pro-Val-p-nitroanilide (BACHEM L-1770) were obtained from BACHEM (King of Prussia, Pa.).

Human α-thrombin, and human factor Xa were obtained from Enzyme Research Laboratories (South Bend, Indiana). Bovine α-chymotrypsin (Sigma C4129), bovine trypsin (Sigma T8642) and human kidney cell urokinase (Sigma U5004) were obtained from Sigma. Human leukocyte elastase was obtained from Elastin Products (Pacific, Mo.). $K_i$ Determinations: All assays are based on the ability of the test compound to inhibit the enzyme catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for $K_m$. Test compounds are prepared as a 1.0 mg/ml solution in DMSO. Dilutions are prepared in DMSO yielding 8 final concentrations encompassing a 200 fold concentration range. Enzyme solutions are prepared at the concentrations listed below in assay buffer.

In a typical $K_i$ determination, into each well of a 96 well plate is pipetted 280 mL of substrate solution, 10 mL of test compound solution, and the plate allowed to thermally equilibrate at 37° C. in a Molecular Devices plate reader for >15 minutes. Reactions were initiated by the addition of a 10 mL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined $K_i$ value.

Thrombin: Thrombin activity was assessed as the ability to hydrolyze the substrate N-succinyl-Ala-Ala-Pro-Arg-p-nitroanilide. Substrate solutions were prepared at a concentration of 32 mM (32 mM<<Km=180 mM) in assay buffer. Final DMSO concentration was 4.3%. Purified human c-thrombin was diluted into assay buffer to a concentration of 15 nM. Final reagent concentrations were: [thrombin]= 0.5 nM, [substrate N-succinyl-Ala-Ala-Pro-Arg-p-nitroanilide]=32 mM.

Factor X [FXa]: FXa activity was assessed as the ability to hydrolyze the substrate N-benzoyl-Ile-Glu-Gly-Arg-p-nitroanilide hydrochloride. Substrate solutions were prepared at a concentration of 51 mM (51<<$K_m$=1.3 mM) in assay buffer. Final DMSO concentration was 4.3%. Purified activated human Factor X was diluted into assay buffer to a concentration of 300 nM. Final reagent concentrations were: [FXa]=10 nM, [N-benzoyl-Ile-Glu-Gly-Arg-p-nitroanilide hydrochloride]=51 mM.

In general, the compounds of the invention demonstrated statistically significant activity against thrombin and/or factor Xa with $K_i$ values for one or both of these enzymes ranging from 0.70 μM to 10 μM. For example, the compound described in Example 2 was found to have K, of 0.70 μM against thrombin and no activity at a concentration of 10 μM against factor Xa. The compound of Example II was found to have a $K_i$ of 1.2 μM against thrombin and a $K_i$ of 2.1 μM against factor Xa. The compound of Example 42 was found to have a $K_i$ of 6.4 μM against thrombin and a $K_i$ of 0.36 μM against factor Xa.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having Formula I:

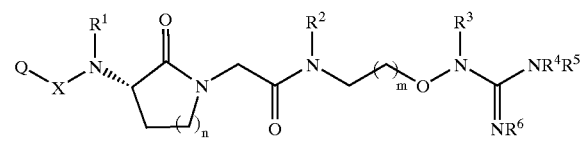

or pharmaceutically acceptable salts thereof; wherein
Q is $C_{6-14}$ aryl, $C_{6-14}$ ar($C_{1-4}$)alkyl, $C_{6-14}$ ar($C_{2-4}$)alkenyl, pyridyl, thienyl, indolyl, quinolinyl, benzothienyl, or imidazolyl; any of which can include one or more optional substituents independently selected from halo, trifluoromethyl, hydroxy, amino, nitro, cyano, $C_{1-3}$ alkoxy, $C_{1-3}$ alkyl, methylenedioxy, carboxyamino, $C_{1-4}$ alkoxycarbonylamino, $C_{6-10}$ aryloxycarbonylamino, $C_{7-11}$ aralkoxycarbonylamino, aminocarbonyl, mono- or di-($C_{1-4}$)alkylaminocarbonyl, acetamido, amidino, pyridyl, naphthyl, pyrimidinyl, alkenyl, mono- or di- ($C_{1-4}$)alkylamino, or combinations thereof;

X is methylene, carbonyl, or sulfonyl;
$R^1$ is hydrogen or $C_{1-3}$ alkyl;
n is 1;
m is 1–4;
$R^2$ is hydrogen or $C_{1-3}$ alkyl;
$R^3$ is hydrogen or $C_{1-3}$ alkyl; and
$R^4$, $R^5$ and $R^6$ are independently hydrogen, hydroxy, $C_{1-6}$ alkyl, $C_{1-6}$ alkoxy, cyano or —$CO_2R^W$, where $R^W$ is $C_{1-4}$ alkyl, $C_{4-7}$ cycloalkyl, benzyl,

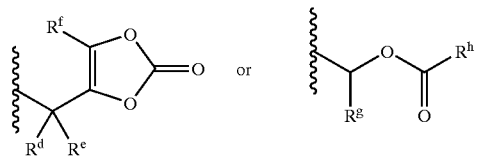

$R^d$, $R^e$ and $R^g$ are each hydrogen, $R^f$ is methyl, and $R^h$ is benzyl or tert-butyl.

2. The compound of claim 1, wherein Q is $C_{6-14}$ aryl, $C_{6-14}$ ar($C_{1-4}$alkyl), $C_{6-14}$ ar($C_{2-4}$alkenyl), or thienyl, any of which can include one or more optional substituents independently selected from the group consisting of halo, trifluoromethyl, hydroxy, amino, nitro, cyano, $C_{1-3}$ alkoxy, $C_{1-3}$ alkyl, methylenedioxy, carboxyamino, $C_{1-4}$ alkoxycarbonylamino, $C_{6-10}$ aryloxycarbonylamino, $C_{7-11}$ aralkoxycarbonylamino, aminocarbonyl, mono- or di- ($C_{1-4}$)alkylaminocarbonyl, acetamido, amidino, pyridyl, naphthyl, pyrimidinyl, alkenyl, mono- or di-($C_{1-4}$)alkylamino, and combinations thereof.

3. The compound of claim 2, wherein Q is phenyl or biphenyl, any of which can include one or more optional substituents independently selected from the group consisting of halo, trifluoromethyl, hydroxy, amino, nitro, cyano, $C_{1-3}$ alkoxy, $C_{1-3}$ alkyl, methylenedioxy, carboxyamino, $C_{1-4}$ alkoxycarbonylamino, $C_{6-10}$ aryloxycarbonylamino, $C_{7-11}$ aralkoxycarbonylamino, aminocarbonyl, mono- or di- ($C_{1-4}$)alkylaminocarbonyl, acetamido, amidino, pyridyl, naphthyl, pyrimidinyl, alkenyl, mono- or di- ($C_{1-4}$) alkylamino, and combinations thereof.

4. The compound of claim 2, wherein Q is 4-(2-methylphenyl)phenyl, 4-(2-methoxyphenyl)phenyl, 4-(3-chlorophenyl)phenyl, 4-(3-fluorophenyl)phenyl, 4-(3-methoxyphenyl)phenyl, 4-(4-fluorophenyl)phenyl, 4-(4-methylphenyl)phenyl, 4-(4-methoxyphenyl)phenyl, 4-(2,4-difluorophenyl)phenyl, 4-(3,4-dichlorophenyl)phenyl, 4-(3,4-dimethoxyphenyl)phenyl, 4-naphth-2-ylphenyl, 4-pyrid-4-ylphenyl, 4-pyrid-2-ylphenyl, biphenyl, 4-(4-chlorophenyl)phenyl, 4-pyrimidin-5-ylphenyl, or 5-(pyrid-5-yl)thien-2-yl.

5. The compound of claim 4, wherein X is $SO_2$.

6. The compound of claim 1, where $R^1$, $R^2$, and $R^3$ are independently selected from the group consisting of hydrogen, methyl, ethyl, n-propyl and isopropyl.

7. The compound of claim 1, where $R^1$, $R^2$, and $R^3$ are hydrogen.

8. The compound of claim 1, where $R^4$, $R^5$, and $R^6$ are independently selected from the group consisting of hydrogen, methyl, ethyl, propyl, n-butyl hydroxy, methoxy, ethoxy, cyano, —$CO_2CH_3$, —$CO_2CH_2CH_3$, and —$CO_2CH_2CH_2CH_3$ 9. The compound of claim 1, where $R^4$, $R^5$ and $R^6$ are each hydrogen.

10. The compound of claim 1, wherein m is 1 or 2.

11. The compound of claim 1, wherein $R^W$ is $C_{1-4}$ alkyl, $C_{4-7}$ cycloalkyl, or benzyl.

12. The compound of claim 1, wherein Q is 4-ethenylphenyl.

13. The compound of claim 1, wherein:

Q is phenyl, biphenyl, naphthyl, benzyl, phenethyl, naphthylmethyl, or thienyl, any of these groups being optionally substituted by one to three optional substituents independently selected from halo, trifluoromethyl, hydroxy, amino, nitro, cyano, $C_{1-3}$ alkoxy, $C_{1-3}$ alkyl, methylenedioxy, carboxyamino, $C_{1-4}$ alkoxycarbonylamino, $C_{6-10}$ aryloxycarbonylamino, $C_{7-11}$aralkoxycarbonylamino, aminocarbonyl, mono- or di-($C_{1-4}$)alkylaminocarbonyl, acetamido, amidino, pyridyl, naphthyl, pyrimidinyl, alkenyl, mono- or di-($C_{1-4}$)alkylamino;

X is carbonyl or sulfonyl;
n is 1;
m is 1 or 2;
$R^1$, $R^2$ and $R^3$ are hydrogen; and
$R^4$, $R^5$ and $R^6$ are independently hydrogen, hydroxy, $C_{1-6}$ alkyl, $C_{1-6}$ alkoxy, cyano or —$CO_2R^W$, $R^W$ is $C_{1-4}$alkyl, $C_{4-7}$cycloalkyl, benzyl,

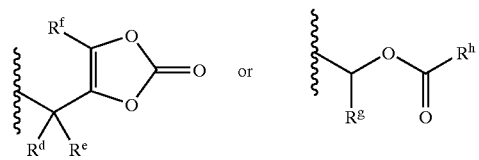

$R^d$, $R^e$ and $R^g$ are each hydrogen, $R^f$ is methyl, and $R^h$ is benzyl or tert-butyl.

14. The compound of claim 13, wherein m is 1.
15. The compound of claim 13, wherein X is sulfonyl.
16. The compound of claim 13, wherein $R^W$ is $C_{1-4}$ alkyl, $C_{4-7}$ cycloalkyl, or benzyl.

17. A compound having Formula I:

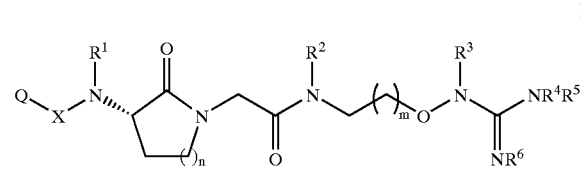

I or pharmaceutically acceptable salts thereof; wherein

Q is naphth-1-yl, naphth-2-yl, 5-dimethylaminonaphth-1-yl, 6-chloronaphth-2-yl, 6-bromonaphth- 2-yl, benzyl, 2-nitrobenzyl, phenyl, 2-methylphenyl, 3-methylphenyl, 4-(n-propyl)phenyl, 4-(t-butyl) phenyl, 4-(t-amyl)phenyl, 4-methoxyphenyl, 4-iodophenyl, 4-fluorophenyl, 4-chlorophenyl, 3,4-dichlorophenyl, 4-nitrophenyl, 4-methylphenyl, 4-ethylphenyl, 3,4-dimethoxyphenyl, or 2-phenylethenyl;

X is methylene, carbonyl, or sulfonyl;
$R^1$ is hydrogen or $C_{1-3}$ alkyl;
n is 1;
m is 1–4;
$R^2$ is hydrogen or $C_{1-3}$ alkyl;
$R^3$ is hydrogen or $C_{1-3}$ alkyl; and
$R^4$, $R^5$ and $R^6$ are independently hydrogen, hydroxy, $C_{1-6}$ alkyl, $C_{1-6}$ alkoxy, cyano or —$CO_2R^W$, $R^W$ is $C_{1-4}$ alkyl, $C_{4-7}$ cycloalkyl, benzyl,

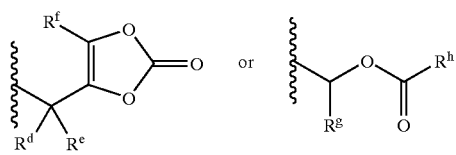

$R^d$, $R^e$ and $R^g$ are each hydrogen, $R^f$ is methyl, and $R^h$ is benzyl or tert-butyl.

18. The compound of claim 17, wherein m is 1 or 2.
19. The compound of claim 17, wherein m is 1.
20. A pharmaceutical composition comprising a compound of claim 1; and a pharmaceutically acceptable carrier or diluent.
21. A method of treating a factor Xa mediated condition in a mammal, comprising administering to a mammal in need of said treatment a therapeutically or prophylactically effective amount of a compound of claim 1.
22. A method of treating thrombosis, ischemia, stroke, restenosis or inflammation comprising administering to a mammal in need of said treatment a therapeutically or prophylactically effective amount of a compound of claim 1.
23. A method of inhibiting coagulation on or in a medical device, comprising contacting, embedding, or linking a compound of claim 1 to a medical device.

24. A method of making a compound of claim 1, comprising:

coupling or condensing a compound of Formula II:

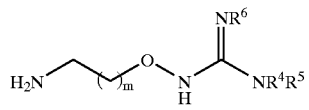

II or a salt thereof, where $R^4$, $R^5$ and $R^6$ are as defined as in claim 1 or optionally protected, and m is 1–4, with a compound of Formula III:

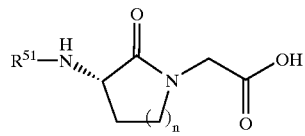

III where $R^{51}$ is H or Q-X.

* * * * *